(12) United States Patent
Anderson, Jr.

(10) Patent No.: US 10,130,122 B2
(45) Date of Patent: Nov. 20, 2018

(54) SUPPLY ITEM FOR VAPOR GENERATING DEVICE

(71) Applicant: Funai Electric Co., Ltd., Osaka (JP)

(72) Inventor: James D. Anderson, Jr., Lexington, KY (US)

(73) Assignee: FUNAI ELECTRIC CO., LTD. (JP)

( * ) Notice: Subject to any disclaimer, the term of this patent is extended or adjusted under 35 U.S.C. 154(b) by 0 days.

(21) Appl. No.: 15/336,863

(22) Filed: Oct. 28, 2016

(65) Prior Publication Data

US 2018/0116281 A1     May 3, 2018

(51) Int. Cl.
A24F 47/00 (2006.01)
A61M 11/04 (2006.01)
A61M 15/00 (2006.01)
A61M 15/06 (2006.01)

(52) U.S. Cl.
CPC ......... *A24F 47/008* (2013.01); *A61M 11/042* (2014.02); *A61M 15/0021* (2014.02); *A61M 15/0065* (2013.01); *A61M 15/06* (2013.01); *A61M 2205/123* (2013.01); *A61M 2205/75* (2013.01); *A61M 2205/8206* (2013.01)

(58) Field of Classification Search
CPC ..... A24F 47/008; A61M 11/042; A61M 15/06
See application file for complete search history.

(56) References Cited

U.S. PATENT DOCUMENTS

| | | | |
|---|---|---|---|
| 6,155,268 A * | 12/2000 | Takeuchi | A24F 47/008 131/194 |
| 9,055,617 B2 | 6/2015 | Thorens et al. | |
| 9,351,522 B2 | 5/2016 | Safari | |
| 2005/0016550 A1 * | 1/2005 | Katase | A24F 47/002 131/194 |
| 2008/0241255 A1 | 10/2008 | Rose et al. | |
| 2009/0188494 A1 * | 7/2009 | Imai | A61M 15/0085 128/203.12 |
| 2009/0223515 A1 * | 9/2009 | Watanabe | A61M 11/00 128/203.15 |
| 2009/0260624 A1 * | 10/2009 | Wada | A61M 15/00 128/203.12 |
| 2010/0206307 A1 * | 8/2010 | Imai | A61M 11/007 128/203.14 |
| 2010/0282254 A1 * | 11/2010 | Takei | B05B 11/02 128/203.12 |
| 2011/0265806 A1 * | 11/2011 | Alarcon | A24F 47/00 131/273 |
| 2013/0087160 A1 | 4/2013 | Gherghe | |
| 2014/0096782 A1 | 4/2014 | Ampolini et al. | |
| 2014/0261500 A1 | 9/2014 | Park | |
| 2015/0114409 A1 | 4/2015 | Brammer et al. | |
| 2015/0128966 A1 | 5/2015 | Lord | |

(Continued)

*Primary Examiner* — Tulsidas C Patel
*Assistant Examiner* — Marcus Harcum
(74) *Attorney, Agent, or Firm* — Ludeka Neely Group, PC

(57) ABSTRACT

A fluid supply, can ridge fir a vapor generating device that includes an ejection head structure and a fluid reservoir body for removable attachment to the ejection head structure. The ejection head structure contains an ejection head and a flexible circuit attached to an ejection head structure for electrical communication with the ejection head. The fluid reservoir body includes a vaporizing fluid therein, a fluid supply port in fluid flow communication with the vaporizing fluid, and a fluid port seal for the fluid supply port.

17 Claims, 9 Drawing Sheets

(56) References Cited

U.S. PATENT DOCUMENTS

| | | | |
|---|---|---|---|
| 2015/0136153 A1* | 5/2015 | Lord | A24F 47/008 |
| | | | 131/328 |
| 2015/0136158 A1 | 5/2015 | Stevens et al. | |
| 2015/0245660 A1* | 9/2015 | Lord | A24F 47/008 |
| | | | 131/328 |
| 2015/0257447 A1* | 9/2015 | Sullivan | A24F 47/008 |
| | | | 131/329 |
| 2015/0367366 A1* | 12/2015 | Edwards | A23G 1/50 |
| | | | 239/302 |
| 2016/0192708 A1* | 7/2016 | DeMeritt | H05B 3/40 |
| | | | 131/329 |
| 2016/0309789 A1* | 10/2016 | Thomas, Jr. | A24F 47/008 |
| 2017/0027226 A1* | 2/2017 | Mironov | A24F 47/008 |
| 2017/0105451 A1* | 4/2017 | Fornarelli | A24F 47/008 |
| 2018/0184722 A1* | 7/2018 | Murison | F04B 43/046 |

* cited by examiner

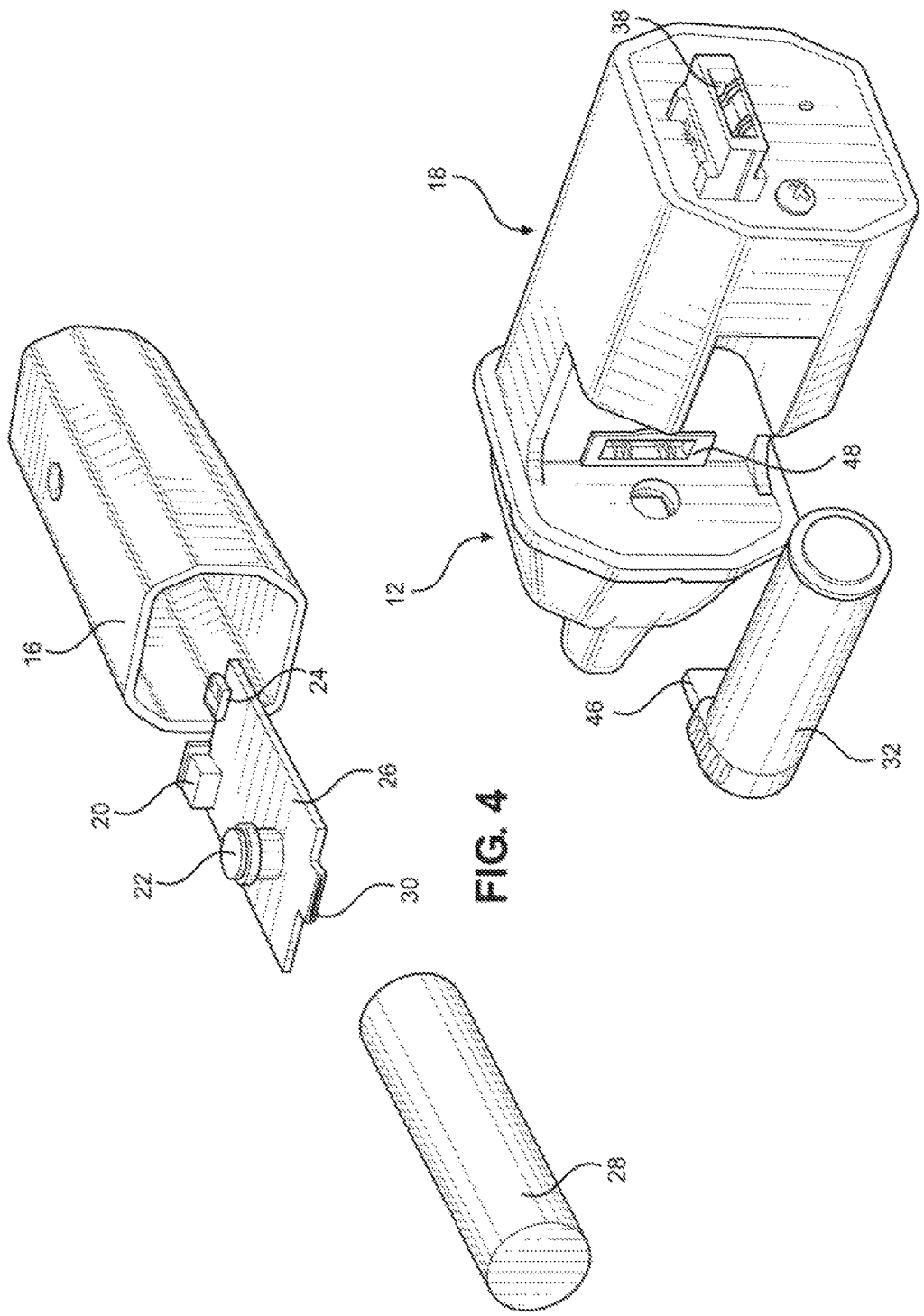

SUPPLY ITEM FOR VAPOR GENERATING DEVICE

TECHNICAL FIELD

One of the applications of a microfluidic ejection device is to jet a solution on to another device where a secondary function may be performed. A common secondary function is to vaporize a solution using a heater such that the contents of the solution can be vaporized so as to deliver the solution as a gaseous substance. Applications of such technology include, but are not limited to, metering and vaporizing device for electronic cigarettes, vapor therapy, gaseous pharmaceutical delivery, vapor phase reactions for microlabs, and the like. This disclosure is directed to a two-piece supply item for a vapor generating, device.

BACKGROUND AND SUMMARY

Vapor generating devices such as electronic cigarettes and vapor therapy devices, among other vapor generating devices include replaceable fluid supply cartridges. Each fluid supply cartridge includes a fluid reservoir and an ejection head. Once the fluid supply is exhausted, the fluid supply cartridge is removed from the vapor generating device and replaced with a fresh fluid supply cartridge. However, the ejection head of the fluid supply cartridge is typically still usable but will be replaced when the fluid supply cartridge is replaced. Since the ejection head is the most expensive part of the fluid supply cartridge, a means for using the ejection head with multiple fluid supply reservoirs is needed.

In view of the foregoing, one embodiment of the disclosure provides a fluid supply cartridge for a vapor generating device. The fluid supply, cartridge includes an ejection head structure and a fluid reservoir body for removable attachment to the ejection head structure. The ejection head structure contains an ejection head and a flexible circuit attached to the ejection head structure for electrical communication with the ejection head. The fluid reservoir body includes a vaporizing fluid therein, a fluid supply port in fluid flow communication with the vaporizing fluid, and a fluid port seal adjacent to the fluid supply port.

Another embodiment of the disclosure provides a cartridge kit for a vaporizing device. The cartridge kit includes an ejection head structure and a plurality of fluid reservoir bodies for removable attachment to the ejection head structure. The ejection head structure contains an ejection head and a flexible circuit attached to the ejection head structure for electrical communication with the ejection head. Each of the fluid reservoir bodies includes a vaporizing fluid therein, a fluid supply port in fluid flow communication with the vaporizing fluid, and a fluid port seal adjacent to the fluid supply port.

A further embodiment of the disclosure provides a vaporizing device having a housing body, a mouthpiece attached to the housing body, a heater assembly disposed in the mouthpiece for vaporizing fluid ejected from an ejection head, and a fluid supply cartridge kit for the vapor generating device. The fluid supply cartridge kit contains an ejection head structure and at least one fluid reservoir body for removable attachment to the ejection head structure, wherein the ejection head structure includes the ejection head and a flexible circuit attached to the ejection head structure for electrical communication with the ejection head. The at least one fluid reservoir body contains a vaporizing fluid therein, a fluid supply port in fluid flow communication with the vaporizing fluid, and a fluid port seal adjacent to the fluid supply port.

In some embodiments, the fluid reservoir body has a removable plug disposed in the fluid supply port thereof for shipping and storing the fluid reservoir body.

In another embodiment, the fluid reservoir body has a first vent hole in the removable plug and a second vent in a cover for the fluid reservoir body. In another embodiment, a removable tape is attached to the removable plug for covering the first vent hole in the removable plug and the second vent in the cover.

In some embodiments, the fluid supply cartridge kit includes two or more fluid reservoir bodies for removable attachment to a single ejection head structure.

In other embodiments, the fluid reservoir body further includes at least one foam insert therein for fluid back-pressure control. In some embodiments, the fluid reservoir body contains a first foam insert having a first density and a second foam insert having a second density greater than the first density.

In some embodiments, the ejection head structure includes a fluid filter, attached to a filter tower structure for filtering fluid flowing from the fluid reservoir body to the ejection head.

A primary advantage of the disclosed embodiments is the ability to, reuse the ejection head for multiple fluid reservoir bodies thereby significantly reducing the cost of replaceable fluid supply cartridges for vaporizing devices. Depending on the size of the fluid reservoir bodies, the ejection head structure may be able to be used with up to 10 or more fluid reservoir bodies before requiring replacement of the ejection head structure.

BRIEF DESCRIPTION OF THE DRAWINGS

Other features and advantages of the inventive may be evident by reference to the following detailed description, drawings and claims wherein:

FIG. 4 is an exploded perspective view, not to scale, of interior components of the housing body of FIG. 2;

FIG. 5 is a perspective view, not to scale, of the removable vapor ejection assembly and a removable fluid supply cartridge for the vapor ejection assembly;

DETAILED DESCRIPTION OF EMBODIMENTS

Figure 1A:
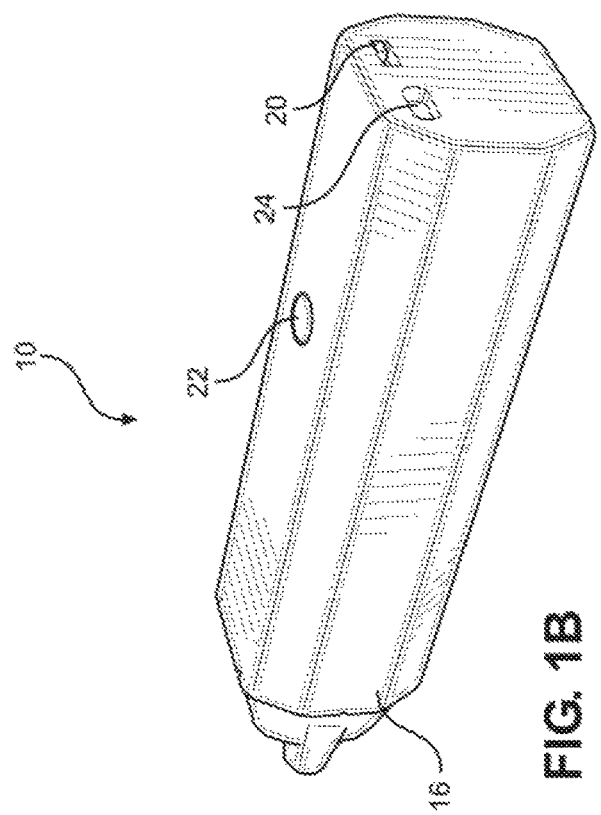
FIGS. 1A-1B are perspective views, not to scale, of a vaporizing device according to the disclosure.
Figure 1B:
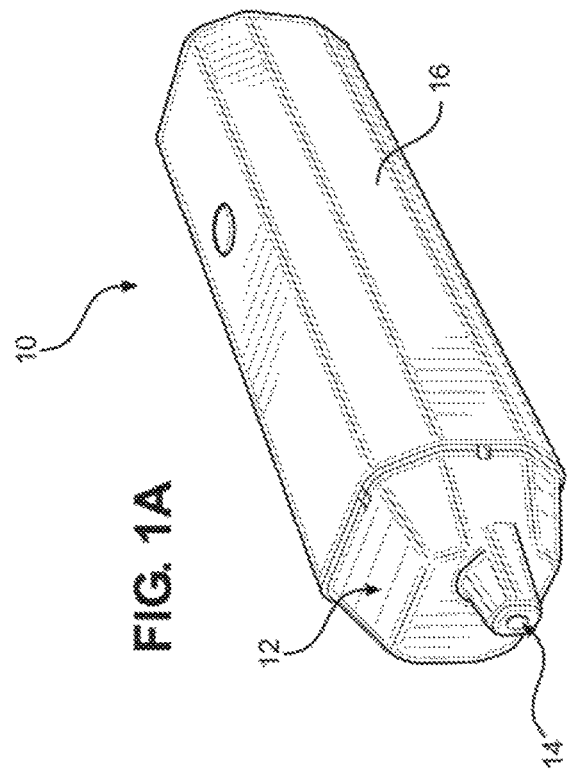
Figure 2:
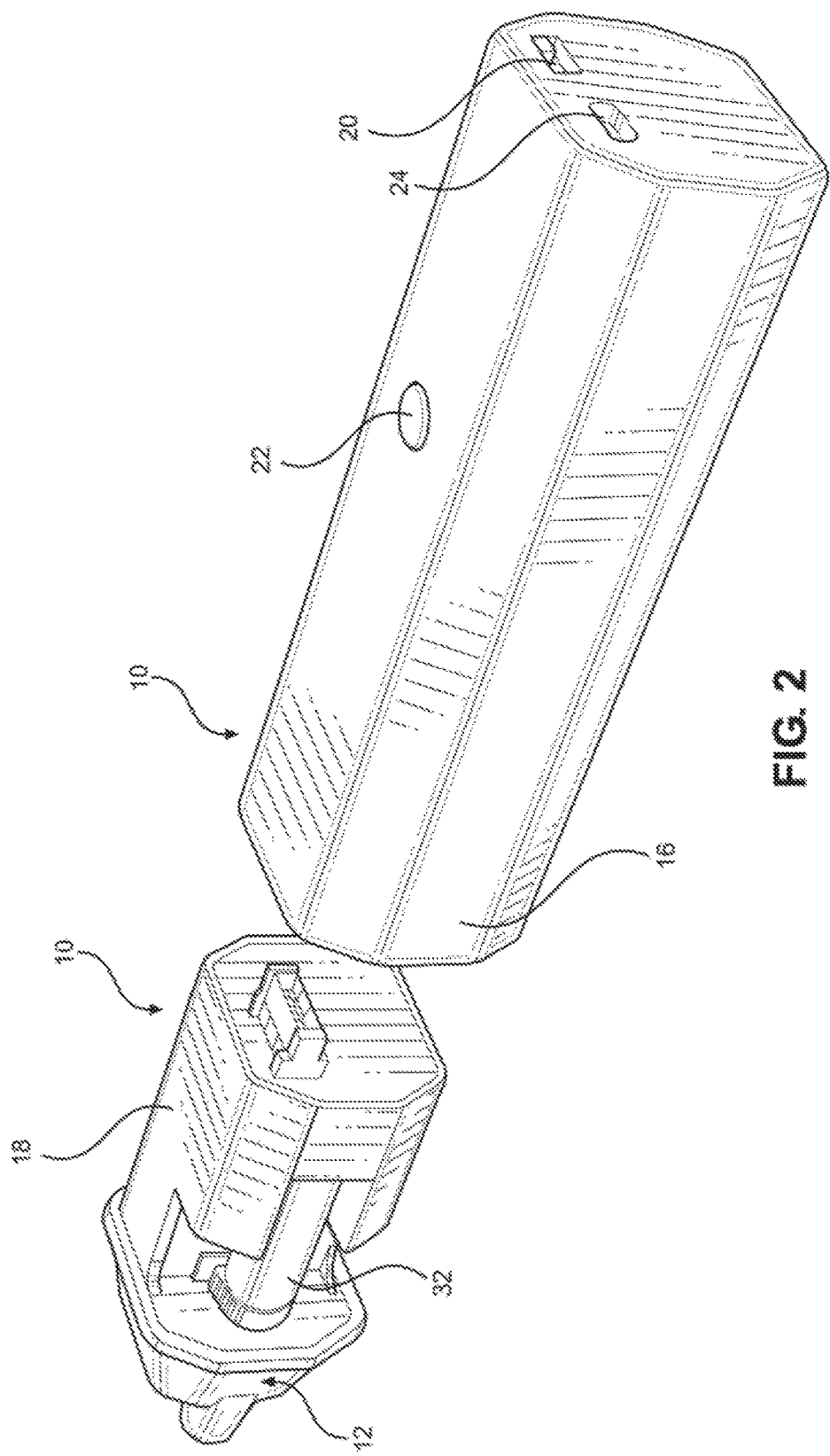
FIG. 2 is art exploded perspective view, not to scale, of the vaporizing device of FIG. 1 showing two main pieces including a housing body, and a removable vapor ejection assembly.

The disclosure is directed to a vaporizing device 10 as shown in FIG. 1 and components therefor as shown in FIG. 2. Such device 10 may be used for a wide variety of applications wherein a liquid is ejected onto a vaporizing heater to provide a vapor stream as described in more detail below. Such devices 10 are typically hand held devices such as electronic cigarettes that have a mouthpiece 12 for inhaling vapors generated by the device 10. The mouthpiece 12 may include a vapor exit conduit 14 for flow of vapors out of the device 10. The main components of the device 10 include a housing body 16 and a removable vapor ejection assembly 18 (FIG. 2). The vaporizing device 10 typically includes a power switch 20, a vapor activation switch 22, and an alternative USB connection 24.

The mouthpiece 12, as well as the body 16 of the vaporizing device 10 may be made from a wide variety of materials including plastics, metals, glass, ceramic and the like provided the materials are compatible with the fluids to be ejected and vaporized by the device 10. A particularly suitable material may be selected from polyvinyl chloride, high density polyethylene, polycarbonate, stainless steel, surgical steel, nickel-plated steel, and the like. All parts, including the mouthpiece 12, and body 16 that come in contact with fluids and vapors may be made of plastic. The vapor exit conduit 14 may be made of metal such as stainless steel or other material that is resistant to heat and vapors generated by the device.

Figure 3:
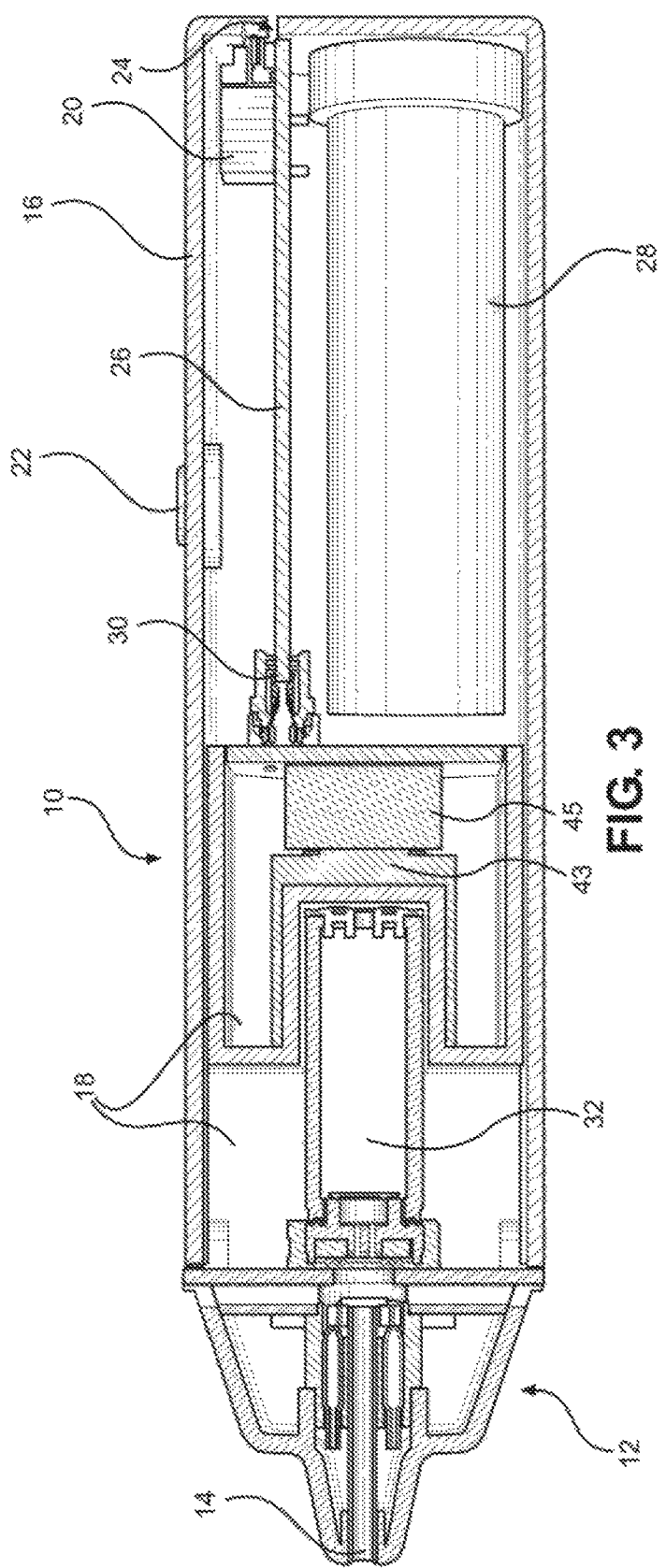
FIG. 3 is a cross-sectional view, not to scale, of the vaporizing device of FIG. 1.

A cross sectional view of die device 10 is shown in FIG. 3 and an exploded view of the housing body 16 is shown in FIG. 4. As shown in FIGS. 3 and 4, the housing body 16 may include a circuit board 26 for providing the logic circuitry for the vaporizing heater and ejection head (described in more detail below). The circuit board 26 is in electrical communication with the vapor ejection assembly 18, the power switch 20 and the USB connection 24. A power source such as a rechargeable battery 28 may also be housed in the housing body 16. Electrical contacts 30 (FIG. 4) may be provided on the circuit board 26 for electrical communication with the removable vapor ejection assembly 18. The USB connection 24 may be used to recharge the battery 28 and/or to change program settings for the ejection head and vaporizing heater.

Figure 6:
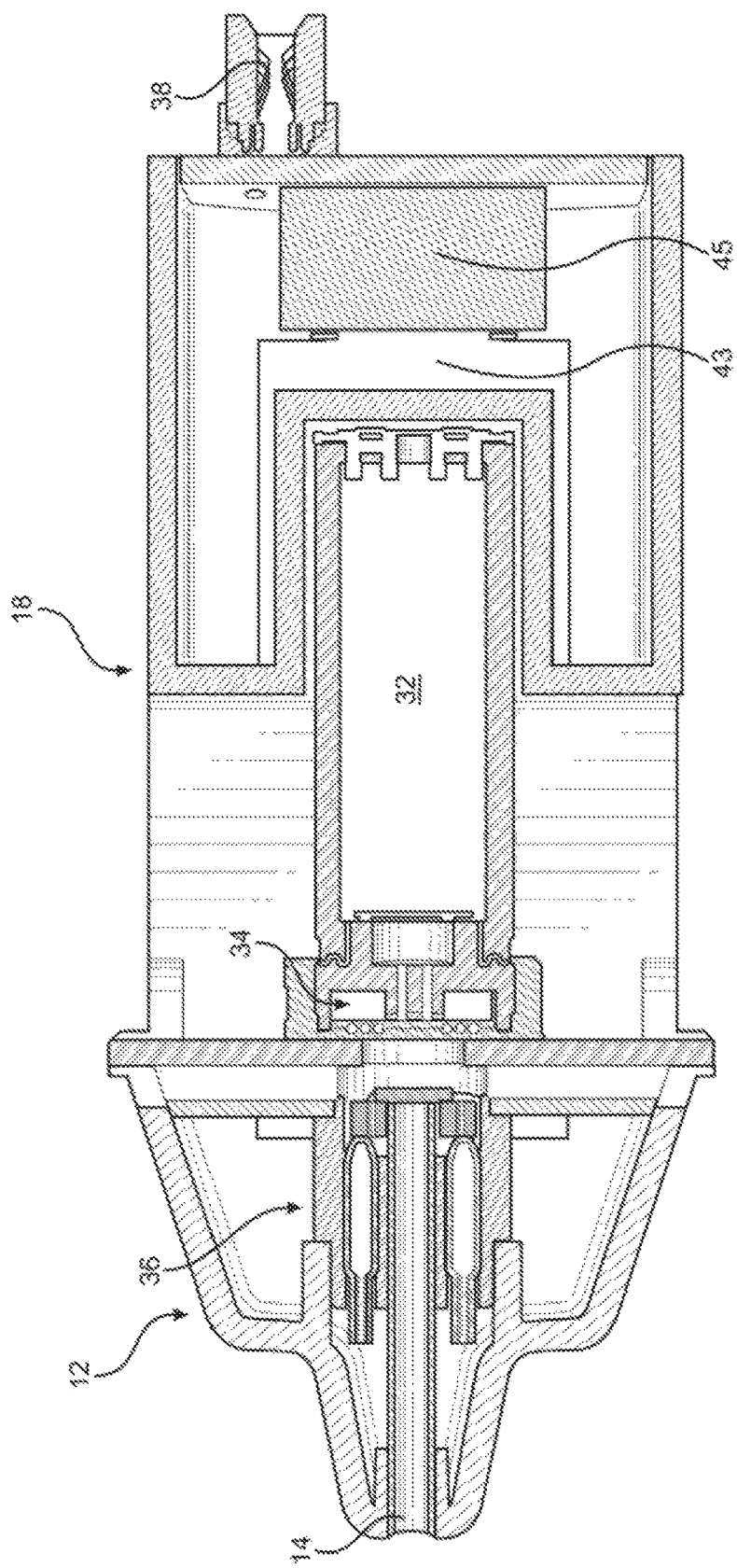
FIG. 6 is a cross-sectional view, not to scale, of the removable vapor ejection assembly of FIG. 5.
Figure 7:
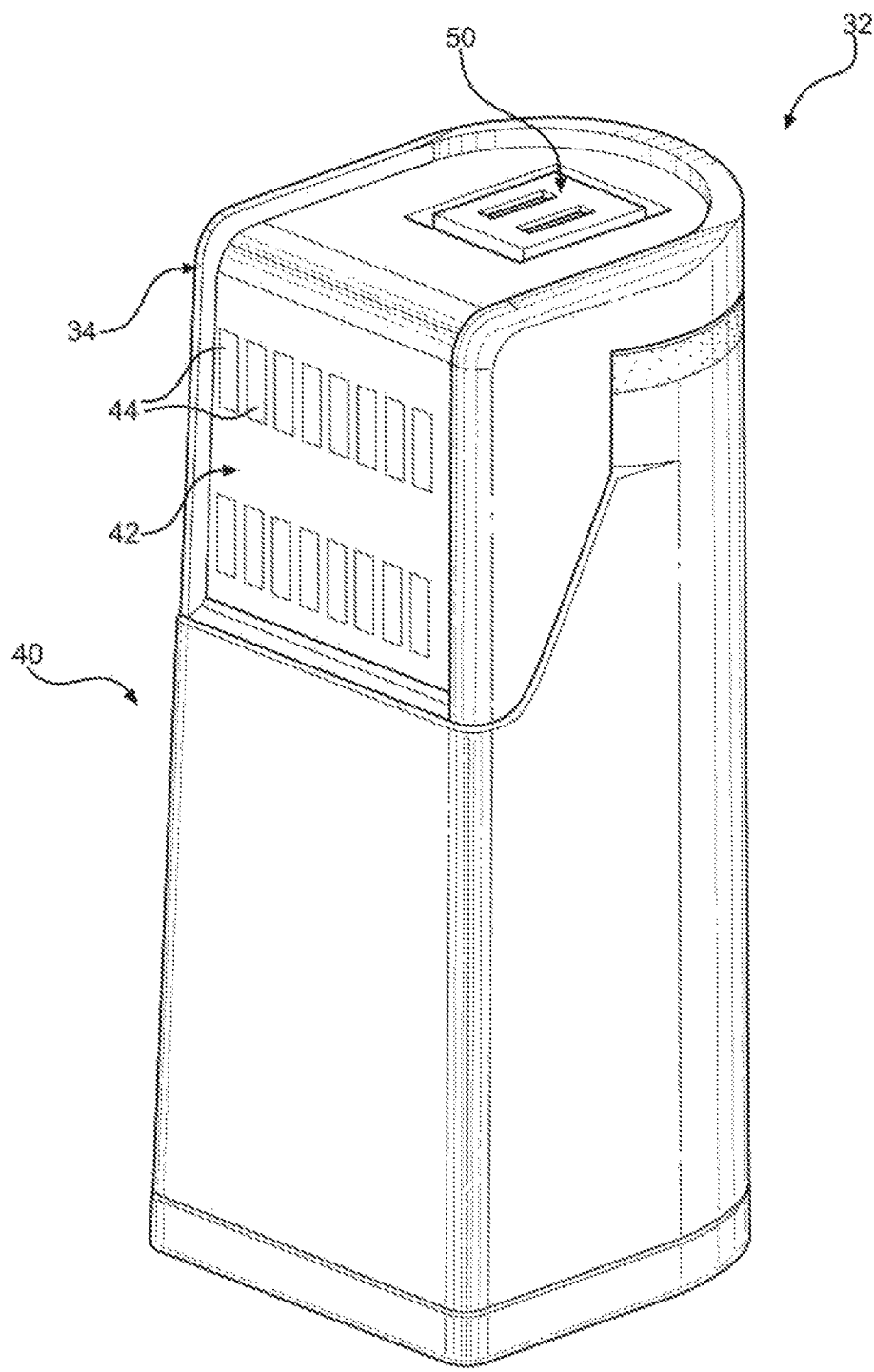
FIG. 7 is a perspective view, not to scale, of a fluid supply cartridge according to an embodiment of the disclosure.

An important component of the vaporizing device is the removable vapor ejection assembly 18 shoe in more detail in FIGS. 5, 6 and 7. The removable vapor ejection assembly 18 includes a removable fluid supply cartridge 32 that supplies fluid to be jetted and vaporized by components of the vapor ejection assembly 18. The fluid supply cartridge 32 has an ejection head structure 34 that is disposed adjacent to a heater assembly 36 component of the vapor ejection assembly 18 and provides fluid to be vaporized by the heater assembly 36. An electrical connector 38 is provided on the removable vapor ejection assembly 18 for electrical connection to the circuit board 26 disposed in the housing body 16 for providing power to the ejection head structure 34 through a flexible circuit 42 on the ejection head structure 34. Power is provided to the ejection head structure 34 on the fluid supply cartridge 32 by a circuit board 43 that is in electrical power communication with a female plug 48 for the fluid supply cartridge 32. An electrical connector 45 is provided for connecting the circuit board 43 to the power source in the housing body 16. The circuit board 43 may also provide power from the battery 28 to the vaporizing heater in the heater assembly 36.

Figure 8:
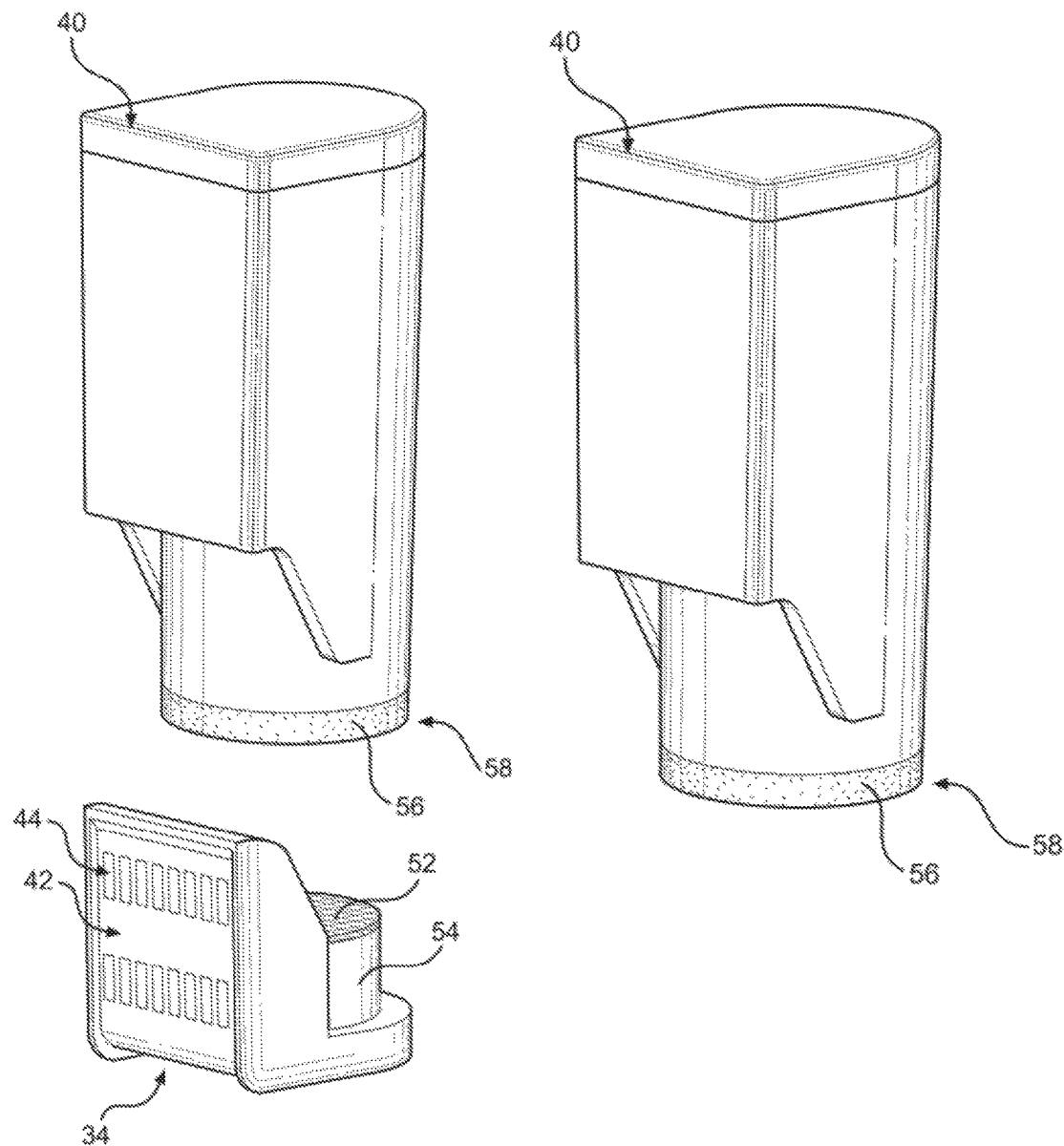
FIG. 8 is a perspective view, not to scale, of a cartridge kit for a vaporizing device comprising an ejection head structure and a plurality of fluid reservoir bodies according to an embodiment of the disclosure.

As shown in FIGS. 7 and 8, the fluid supply partridge 32 is primarily a two-piece item that includes an ejection head structure 34 and a fluid reservoir body 40. That is, each piece 34 and 40 is an assembly of components, as described in more detail below, that can be separately removed and replaced as needed for the vaporizing device 10. Accordingly, the ejection head structure 34 may be used with multiple fluid reservoir bodies 40, such as two or more reservoir bodies 40, desirably from about two to ten or more fluid reservoir bodies 40. Depending on the fluid being vaporized, the ejection head structure 34 may be expected to be used, with at least five or more fluid reservoir bodies 40. Accordingly, a cartridge kit containing an ejection head structure 34 and five or more fluid reservoir bodies 40 may be sold for use with a vaporizing device 10 according to the disclosure.

The ejection head structure 34 may include the flexible circuit 42 containing a plurality of electrical, contacts 44 for electrical communication with the vapor ejection assembly 18. In another embodiment, a male plug 46 may be included on the ejection head structure 34 for electrical communication with the female plug 48 on the vapor ejection assembly 18 as shown in FIG. 5. The flexible circuit 42, and/or male and male and female plugs, are in electrical communication with an ejection head 50 that is attached to the ejection head structure 34.

As shown in FIG. 8, the ejection head structure 34 includes a filter 52 and a filter tower 54 that provides fluid from the fluid reservoir body 40 through a fluid supply port 57 (FIG. 10) to the ejection head structure 34. In order to provide a fluid tight connection between the ejection head structure 34 and the fluid reservoir body 40, a fluid port seal 56 is provided adjacent to one end 58 of the fluid reservoir body 40. The seal 56 may be an o-ring seal made of a wide variety of elastomeric materials, including but not limited to natural or synthetic rubber, ethylene/propylene diene monomer, fluoropolymer elastomeric materials and the like. Materials that are resistant to the fluids in the fluid reservoir body 40 are particularly suitable for use as the fluid port seal 56.

Figure 9:
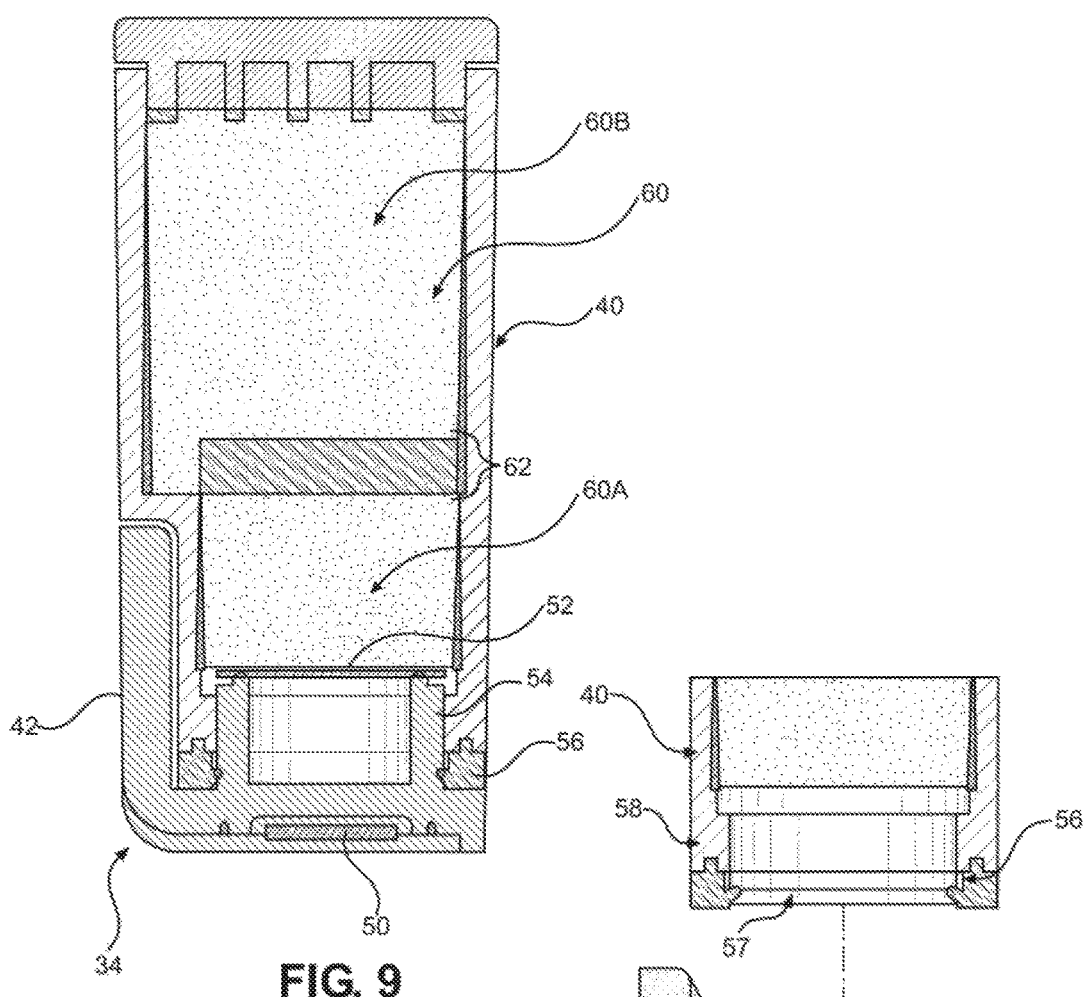
FIG. 9 is a cross-sectional view, not to scale, of the fluid supply cartridge of FIG. 7.
Figure 10:
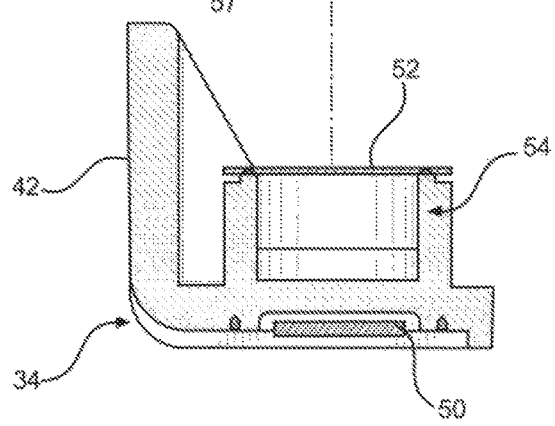
FIG. 10 is a cross-sectional, exploded view, of the ejection head structure and a portion of the fluid reservoir body of FIG. 9.

Further details of the fluid reservoir body 40 and ejection head structure are illustrated in FIGS. 9 and 10. In FIG. 9, the ejection head structure 34 is sealingly connected to the fluid reservoir body 40 by fluid port seal 56. The fluid reservoir body 40 may contain only fluid to be vaporized by the vaporizing device 10. However, in order to maintain a sufficient back pressure on the ejection head 50, a compressible fluid permeable body 60 may be located within the fluid reservoir body. The compressible fluid permeable body 60 may include one or more foam or felt materials. In one embodiment, the compressible permeable body 60 includes a first compressible fluid permeable body 60A and a second compressible permeable body 60B. In one embodiment, the compressible fluid permeable body 60 may be a hydrophilic foam made from melamine. When the ejection head structure 34 is attached to the fluid reservoir body 40, the filter 52 of the ejection head structure 34 is in contact with the compressible fluid permeable body 60A so that fluid stored in the fluid permeable body 60 travels through the permeable body 60 to the filter 52, and through the filter 52 to the filter tower 54 and then to the ejection head 50.

In one embodiment, the compressible fluid permeable body 60 may include a relatively high density felt or foam 60A and a relatively lower density felt or foam 60B. In other embodiments, the fluid permeable body 60A may be hydrophilic and the fluid permeable body 60B may be hydrophobic. In other embodiments, both fluid permeable bodies 60A an 60B may be hydrophilic or hydrophobic. In order to assure fluidic connection between the fluid permeable body 60 and the filler 52, the relatively lower density felt or foam 60B may be compressed against the higher density felt or foam 60A as illustrated by area 62 in FIG. 9. Area 62 represents a portion of the relatively lower density felt or foam 60B that is compressed by the higher density felt or foam 60A so that there is intimate contact between foam 60A and 60B and fluid flow from foam 60B to 60A without a void space or gap therebetween.

Figure 11:
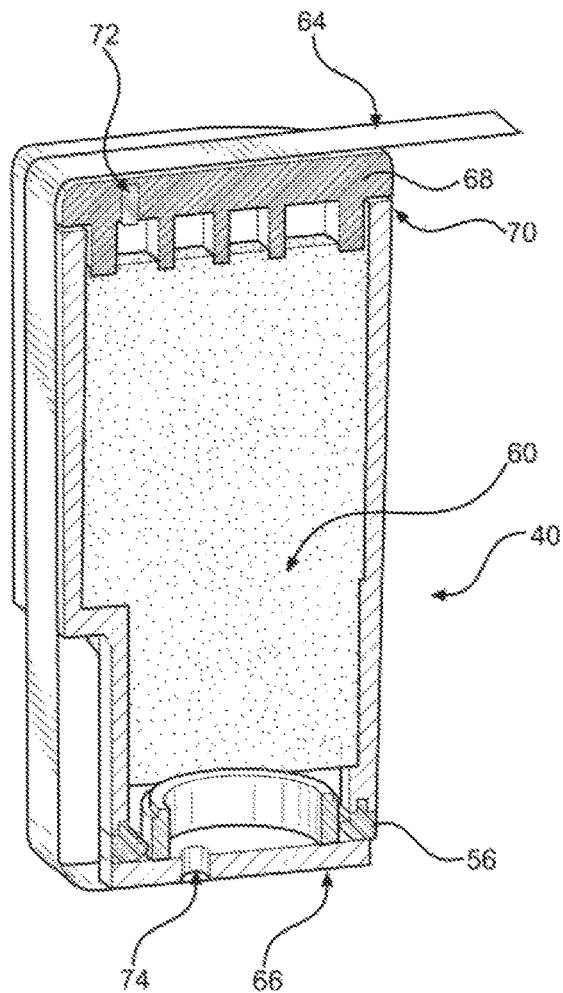
FIG. 11 is a cross-sectional view, not to scale, of a fluid reservoir body containing a removable tape attached to a removable plug in a fluid supply port of the fluid reservoir body.
Figure 12:
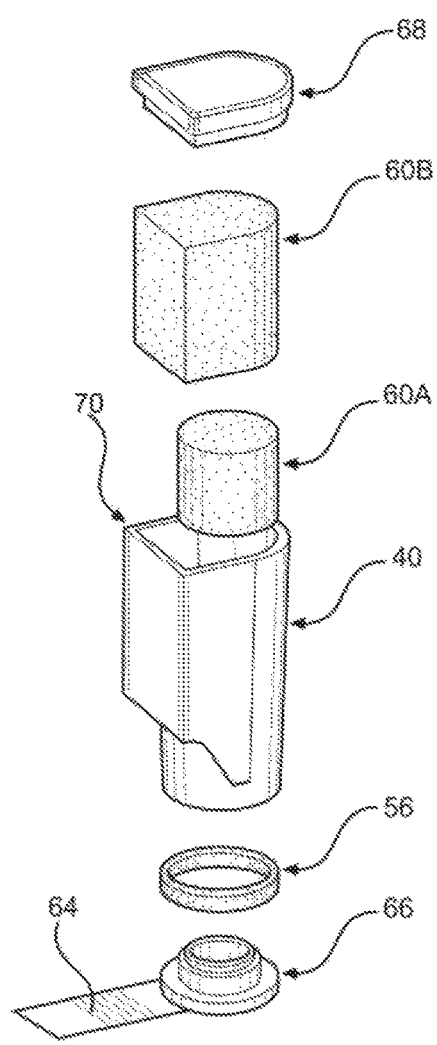
FIG. 12 is an exploded view, not to scale of the fluid reservoir body, tape and plug of FIG. 11.

In order to package the fluid reservoir body 40 separately from the ejection head structure 34, a removable tape 64 and removable plug 66 may be used as illustrated in FIGS. 11 and 12. As shown in FIG. 11, the fluid reservoir body 40 includes a cover 68 that closes a second end 70 of the fluid reservoir body 40. The cover 68 includes a vent 72 that may be a hole and serpentine path to the interior of the fluid reservoir body 40 vent for venting the fluid reservoir body 40 during use. The tape 64 covers the vent 72 in the cover 68 until the reservoir body 40 is ready for use.

The removable plug 66 is also vented by vent hole 74 when the tape 64 is removed, but remains covered during shipping and storage. Also, the tape 64 may be fixedly attached to the removable plug 66 so that removal of the tape 64 will also remove the plug 66 from the fluid reservoir body 40 so that the body 40 can be attached to the ejection head structure 34. In other embodiments, separate tapes may be used for the vent 72 and for removing the plug 66.

Accordingly, embodiments of the disclosure may provide a number of advantages. For example, the ejection head structure 34 is the costliest item of the fluid supply cartridge 32. Hence, the fluid reservoir body 40 may be provided as a separate item at a much lower cost than the entire assembled fluid supply cartridge 32 and the ejection head structure 34 may be used with multiple fluid reservoir body changes. The ability to remove and replace the ejection head structure 34 also may ensure consistent dosing of fluid to the vaporizing device 10 since over time, air and impurities can accumulate in or be caught in ejection nozzles of the ejection head 50 causing the dosage to be less than desirable. Changing the ejection head structure 34 over week or two keeps dosages consistent.

A cartridge kit containing multiple fluid supply bodies 40 and a single ejection head structure 34 may be sold as supply item for the vaporizing device 10.

A single removable tape 64 may be used to cover the vent 72 in the cover 68 and also to cover the vent hole 74 in the removable plug 66. Removal of the tape 64 will not only open the vent 72 and vent hole 74, but will also remove the plug 66 from the fluid reservoir body 40.

The ejection head structure 34 may have a separate latching mechanism to attach the ejection head structure to the vapor ejection assembly 18 so that only the fluid reservoir body 40 is removed from the device 10 for exchange and replacement thereof.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications variations, improvements, and substantial equivalents.

What is claimed is:

1. A fluid supply cartridge comprising an ejection head structure and a fluid reservoir body for removable attachment to the ejection head structure, wherein the ejection head structure comprises an ejection head and a flexible circuit attached to the ejection head structure for electrical communication with the ejection head, and wherein the fluid reservoir body comprises a vaporizing fluid therein, a fluid supply port in fluid flow communication with the vaporizing fluid, a first vent hole in a cover for the fluid reservoir body on a proximal end of the fluid reservoir body, and a fluid port seal adjacent to the fluid supply port, which fluid port seal and fluid supply port are on a distal end of the fluid reservoir body.

2. The fluid supply cartridge of claim 1, wherein the fluid reservoir body further comprises a removable plug disposed in the fluid supply port thereof for shipping and storing the fluid reservoir body, wherein said removable plug is separately removable from the fluid reservoir body.

3. The fluid supply cartridge of claim 2, wherein the fluid reservoir body further comprises a second vent hole in the removable plug.

4. The fluid supply cartridge of claim 3, further comprising a removable tape attached to the removable plug for covering the second vent hole in the removable plug and the first vent in the cover.

5. The fluid supply cartridge of claim 1, wherein the fluid reservoir body further comprises at least one foam insert therein for fluid back-pressure control.

6. The fluid supply cartridge of claim 1, wherein the fluid reservoir body further comprises a first foam insert having a first density and a second foam insert having a second density greater than the first density.

7. The fluid supply cartridge of claim 1, wherein the ejection head structure further comprises a fluid filter attached to a filter tower structure for filtering fluid flowing from the fluid reservoir body to the ejection head.

8. A vaporizing device comprising a mouthpiece, a vapor ejection assembly attached to the mouthpiece and the fluid supply cartridge of claim 1 attached to the vapor ejection assembly.

9. A cartridge kit for a vaporizing device comprising an ejection head structure and a plurality of fluid reservoir bodies for removable attachment to the ejection head structure, wherein the ejection head structure comprises an ejection head and a flexible circuit attached to the ejection head structure for electrical communication with the ejection head, and wherein each of the fluid reservoir bodies comprises a vaporizing fluid therein, a fluid supply port in fluid flow communication with the vaporizing fluid, a first vent hole in a cover for each of the fluid reservoir bodies on a proximal end of the fluid reservoir bodies, and a fluid port seal adjacent to the fluid supply port, which fluid port seal and fluid supply port are on a distal end of the fluid reservoir bodies.

10. The cartridge kit of claim 9, wherein each of the fluid reservoir bodies further comprises a removable plug disposed in the fluid supply port thereof for shipping and storing the fluid reservoir bodies, wherein said removable plug is separately removable from the fluid reservoir bodies.

11. The cartridge kit of claim 10, wherein each of the fluid reservoir bodies further comprises a second vent hole in the removable plug.

12. The cartridge kit of claim 11, further comprising a removable tape attached to the removable plug for covering the second vent hole in the removable plug and the first vent in the cover.

13. A vaporizing device comprising a housing body, a mouthpiece attached to the housing body, a heater assembly disposed in the mouthpiece for vaporizing fluid ejected from an ejection head, and a fluid supply cartridge kit for the vapor generating device, the fluid supply cartridge kit comprising an ejection head structure and at least one fluid reservoir body for removable attachment to the ejection head structure, wherein the ejection head structure comprises the ejection head and a flexible circuit attached to the ejection head structure for electrical communication with the ejection head, and wherein the at least one fluid reservoir body comprises a vaporizing fluid therein, a fluid supply port in fluid flow communication with the vaporizing fluid, a first vent hole in a cover for the fluid reservoir body on a proximal end of the fluid reservoir body, and a fluid port seal adjacent to the fluid supply port, which fluid support seal and fluid supply port are on a distal end of the fluid reservoir body.

14. The vaporizing device of claim 13, wherein the fluid reservoir body further comprises a removable plug disposed in the fluid supply port thereof for shipping and storing the fluid reservoir body, wherein said removable plug is separately removable from the fluid reservoir body.

15. The vaporizing device of claim 14, wherein the fluid reservoir body further comprises a second vent hole in the removable plug.

16. The vaporizing device of claim 15, further comprising a removable tape attached to the removable plug for covering the second vent hole in the removable plug and the first vent in the cover.

17. The vaporizing device of claim 13, wherein the fluid supply cartridge kit comprises two or more fluid reservoir bodies.

* * * * *